(12) United States Patent
Seino et al.

(10) Patent No.: US 12,371,422 B2
(45) Date of Patent: Jul. 29, 2025

(54) FLUORINE-CONTAINING PYRIMIDINE COMPOUND AND MANUFACTURING METHOD FOR SAME

(71) Applicant: UNIMATEC CO., LTD., Tokyo (JP)

(72) Inventors: Junya Seino, Kitaibaraki (JP); Rie Aotsu, Kitaibaraki (JP); Keisuke Kokin, Kitaibaraki (JP)

(73) Assignee: UNIMATEC CO., LTD. (JP)

( * ) Notice: Subject to any disclaimer, the term of this patent is extended or adjusted under 35 U.S.C. 154(b) by 350 days.

(21) Appl. No.: 17/769,389

(22) PCT Filed: Oct. 29, 2020

(86) PCT No.: PCT/JP2020/040661
§ 371 (c)(1),
(2) Date: Apr. 15, 2022

(87) PCT Pub. No.: WO2021/085540
PCT Pub. Date: May 6, 2021

(65) Prior Publication Data
US 2024/0150329 A1 May 9, 2024

(30) Foreign Application Priority Data
Nov. 1, 2019 (JP) ................. 2019-199807

(51) Int. Cl.
*C07D 405/04* (2006.01)
(52) U.S. Cl.
CPC .................. *C07D 405/04* (2013.01)
(58) Field of Classification Search
CPC .......... C07D 405/04; A61P 9/10; A61P 13/12; A61P 31/04; A61P 35/00; A61P 35/02; A61P 35/04; A61P 1/18; A61K 31/506
See application file for complete search history.

(56) References Cited

U.S. PATENT DOCUMENTS

| 3,621,022 A | 11/1971 | Herbert et al. |
| 2005/0075357 A1 | 4/2005 | Zhang et al. |
| 2005/0131232 A1 | 6/2005 | Stossel et al. |
| 2013/0216498 A1 | 8/2013 | Eastwood et al. |
| 2015/0018353 A1 | 1/2015 | Kim et al. |
| 2015/0342954 A1 | 12/2015 | Kim et al. |
| 2021/0403455 A1 | 12/2021 | Seino et al. |

FOREIGN PATENT DOCUMENTS

| CN | 1656195 A | 8/2005 |
| CN | 1871009 A | 11/2006 |
| CN | 104066731 A | 9/2014 |
| CN | 107286146 A | 10/2017 |

(Continued)

OTHER PUBLICATIONS

Second Office Action issued in corresponding Chinese Patent Application No. 202080071319.7 dated Apr. 11, 2024, with English translation (10 Pages).
Office Action issued in corresponding Indian Patent Application No. 202237027396, dated Feb. 13, 2023, with English translation (5 pages).
Yoshio Inoue et al., "A Facile Onepot Preparation of 2-Methyl-and 2-Phenyl-4-Fluoro-5-Trifluoromethyl-6-Methoxypyrimidine from Methyl 2-Hydryl-2-(F-Methyl)-F-Propyl Ether", Journal of Fluorine Chemistry, 27 (1985), pp. 231-236.
PubChem ID: 104798577, Jan. 13, 2016, 9 Pages.
PubChem ID: 53781829, Dec. 4, 2011, 8 Pages.
PubChem ID: 62698335, Oct. 22, 2012, 9 Pages.
Office Action issued in corresponding Chinese Patent Application No. 202080071319.7 dated Nov. 29, 2024, with English translation (14 Pages).

(Continued)

*Primary Examiner* — Joseph K McKane
*Assistant Examiner* — Meghan C Heasley
(74) *Attorney, Agent, or Firm* — Harness, Dickey & Pierce, P.L.C.

(57) ABSTRACT

A fluorine-containing pyrimidine compound is represented by the following formula (1) or (2):

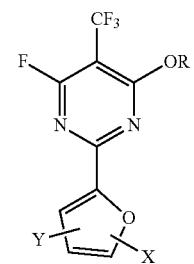

(1)

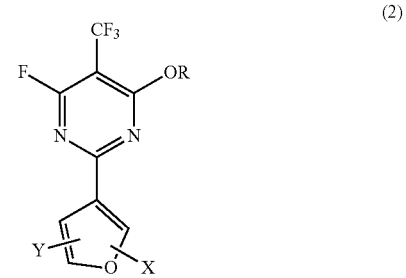

(2)

wherein R represents a hydrocarbon group having 1 to 12 carbon atoms; and X and Y each independently represent a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$, or $-CONA^1A^2$, where $A^1$ and $A^2$ each independently represent a hydrogen atom or a hydrocarbon group having 1 to 10 carbon atoms.

6 Claims, No Drawings

(56) References Cited

FOREIGN PATENT DOCUMENTS

| CN | 108218793 A | 6/2018 | |
|---|---|---|---|
| CN | 108299465 A | 7/2018 | |
| CN | 108503623 A | 9/2018 | |
| JP | S59-104364 A | 6/1984 | |
| JP | 2007-506746 A | 3/2007 | |
| WO | 1998-056789 A1 | 12/1998 | |
| WO | WO-9856789 A1 * | 12/1998 | ............. A01N 43/54 |
| WO | 2020-116296 A1 | 6/2020 | |

OTHER PUBLICATIONS

"Synthesis of Some Novel Furan-tagged Thienopyrimidine Derivatives as Antibacterial Agents" Journal of Heterocyclic Chemistry, 2019, vol. 56, p. 485-492.
"Novel human adenosine receptor antagonists based on the 7-amino-thiazolo[5,4-d]pyrimidine scaffold. Structural investigations at the 2-, 5-and 7-positions to enhance affinity and tune electivity" Bioorganic & Medicinal Chemistry Letters, 2019, vol. 29, p. 563-569.
"Discovery of Reversible DNA Methyltransferase and Lysine Methyltransferase G9a Inhibitors with Antitumoral in Vivo Efficacy" Journal of Medicinal Chemistry, 2018, vol. 61, p. 6518-6545.
"Synthetic molecules for disruption of the MYC protein-protein interface" Bioorganic & Medicinal Chemistry, 2018, vol. 26, p. 4234-4239.
"Discovery of Novel Dual Histone Deacetylase and Mammalian Target of Rapamycin Target Inhibitors as a Promising Strategy for Cancer Therapy" Journal of Medicinal Chemistry, 2019, vol. 62, p. 1577-1592.
"A highly potent and selective inhibitor Roxyl-WL targeting IDO1 promotes immune response against melanoma" Journal of Enzyme Inhibition and Medicinal Chemistry, 2018, vol. 33, p. 1089~p. 1094.
"Catalyst-free and visible light promoted trifluoromethylation and perfluoroalkylation of uracils and cytosines" Chemical Communications, 2018, vol. 54, pp. 13662-13665.
"Visible-Light Photoredox Decarboxylation of Perfluoroarene Iodine(III) Trifluoroacetates for C—H Trifluoromethylation of (Hetero)arenes" ACS Catalysis, 2018, vol. 8, p. 2839-2843.
"Multicomponent Oxidative Trifluoromethylation of Alkynes with Photoredox Catalysis: Synthesis of a-Trifluoromethyl Ketones" Organic Letters, 2018, vol. 20, p. 1693-1697.
"Trifluoromethylation of arenes and heteroarenes by means of photoredox catalysis" Nature, 2011, vol. 480, p. 224-228.
International Search Report for corresponding International Application No. PCT/JP2020/040661 dated Dec. 8, 2020 with English translation (4 Pages).
Written Opinion for corresponding International Application No. PCT/JP2020/040661 dated Dec. 8, 2020, with English translation (8 Pages).
International Preliminary Report on Patentability for corresponding International Application No. PCT/JP2020/040661 dated Dec. 8, 2020, with English translation (9 Pages).
Notification of Reasons for Refusal for corresponding Japanese Application No. 2021-553686 dated May 9, 2022 with English translation (5 Pages).
Office Action issued in corresponding Chinese Patent Application No. 202080071319.7 dated Nov. 1, 2023, with English translation (12 Pages).
A. P. Molchanov et al., Product Subclass 2: "1—Halo-1-(organooxy) alk-1-enes", Science of Synthesis, 24, 2006, 129-166 (38 Pages).
Extended European Search Report issued in corresponding European Patent Application No. 20880565.5 dated Nov. 17, 2023 (9 Pages).

* cited by examiner

FLUORINE-CONTAINING PYRIMIDINE COMPOUND AND MANUFACTURING METHOD FOR SAME

CROSS REFERENCE TO RELATED APPLICATIONS

The present application is a national stage application of International Patent Application No. PCT/JP2020/040661 filed on Oct. 29, 2020, which claims the benefit of Japanese Patent Application No. 2019-199807, filed on Nov. 1, 2019. The contents of both the above applications are hereby incorporated by reference herein in their entireties.

BACKGROUND

Technical Field

The present disclosure relates to a fluorine-containing pyrimidine compound and a method for producing the same.

Related Art

Conventionally, fluorine-containing pyrimidine compounds have been reported to have various biological activities. Among them, a compound having a furan ring structure at the 2-position of the pyrimidine ring is expected to be used in the fields of medicine and agrochemicals.

More specifically, Journal of Heterocyclic Chemistry, 2019, vol. 56, pp. 485-492. reports that a compound having a 2-(furanyl)-pyrimidine structure has an antibacterial activity, and Bioorganic & Medicinal Chemistry Letters, 2019, vol. 29, pp. 563-569. reports that the compound having the 2-(2-furanyl)-pyrimidine structure is effective in treatment of heart failure and kidney failure. Moreover, Journal of Medicinal Chemistry, 2018, vol. 61, pp. 6518-6545.reports the compound having the 2-(2-furanyl)-pyrimidine structure is effective in inhibiting progression of acute myeloid leukemia and tumor metastasis, and Bioorganic & Medicinal Chemistry, 2018, vol. 26, pp. 4234-4239. reports that the compound having the 2-(2-furanyl)-pyrimidine structure has an antitumor activity.

Journal of Medicinal Chemistry, 2019, vol. 62, pp. 1577-1592., Journal of Enzyme Inhibition and Medicinal Chemistry, 2018, vol. 33, pp. 1089-1094., and Chinese Patent Laid-Open No. 108503623 report that a compound having a 2-(3-furanyl)-pyrimidine structure has an antitumor activity, and Chinese Patent Laid-Open No. 108299465 reports that the compound with the 2-(3-furanyl)-pyrimidine structure is effective in treatment of pancreatitis.

Conventionally, methods for synthesizing a pyrimidine compound having a trifluoromethyl group at the 5-position of the pyrimidine ring and substituents at the 4-position and 6-position of the pyrimidine ring have been investigated. More specifically, Chemical Communications, 2018, 54 volumes, pp. 13662-13665. reports a synthetic method using trifluoroiodomethane, ACS Catalysis, 2018, vol. 8, pp. 2839-2843. reports a synthetic method using trifluoroacetic acid, and Organic Letters, 2018, vol. 20, pp. 1693-1697. reports a synthetic method using a 5-(trifluoromethyl)dibenzothiophenium salt (Umemoto reagent). Moreover, Nature, 2011, vol. 480, pp. 224-228. reports a synthetic method using a trifluoromethanesulfonic acid derivative, Chinese Patent Laid-Open No. 107286146 reports a synthetic method using sodium trifluoromethanesulfinate (Langlois reagent), and Chinese Patent Laid-Open No. 108218793 reports a synthetic method using (trifluoromethyl)trimethylsilane (Ruppert reagent).

Technical Problem

For the compound having a 2-furanyl-pyrimidine structure, a compound having substituents at the 4-, 5-, and 6-positions of the pyrimidine ring structure has been promising to further improve a biological activity and structural extensibility thereof.

Conventionally, however, it has been difficult to produce a fluorine-containing pyrimidine compound having a fluorine-containing substituent at the 5-position, a heterocyclic ring substituent at the 2-position, and substituents at the 4-position and 6-position in terms of reactivity and selectivity, whereby such a fluorine-containing pyrimidine compound has not been reported. Therefore, it has been desired to produce a fluorine-containing pyrimidine compound having substituents at the 4-, 5-, and 6-positions and a furan ring structure at the 2-position, and to establish a production method thereof.

Then, the present inventors have discovered that a reaction with specific raw material enables introduction of a furan ring structure at the 2-position between the two nitrogen atoms on the pyrimidine ring, and thus have completed the present disclosure. Namely, the present disclosure provides a novel fluorine-containing pyrimidine compound having substituents at the 4-, 5-, and 6-positions and a furan ring structure as a substituent at the 2-position, which has not been known conventionally, and a method capable of easily producing the fluorine-containing pyrimidine compound.

SUMMARY

The configuration of the present disclosure is as follows.
[1] A fluorine-containing pyrimidine compound represented by the following formula (1) or (2):

[Formula 1]

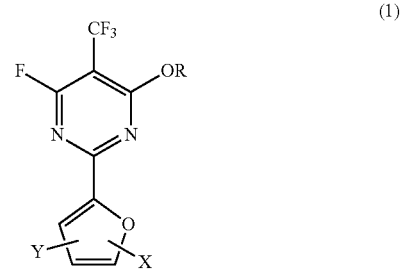

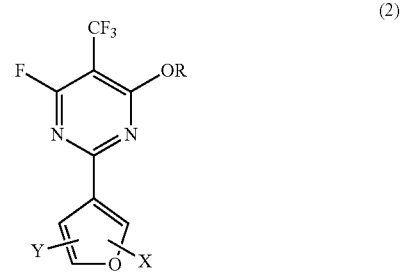

wherein
R represents a hydrocarbon group having 1 to 12 carbon atoms; and
X and Y each independently represent a hydrogen atom, a halogen atom, a hydrocarbon group having 1 to 10 carbon atoms, —$C_nF_{2n+1}$ where n is an integer of 1 to 10, a nitro group, a boronic acid group, —$OA^1$, —$SO_mA^1$ where m is an integer of 0 to 3, —$NA^1A^2$, —$COOA^1$, or —$CONA^1A^2$, where $A^1$ and $A^2$ each independently represent a hydrogen atom or a hydrocarbon group having 1 to 10 carbon atoms.

[2] The fluorine-containing pyrimidine compound according to [1], wherein R is an alkyl group having 1 to 10 carbon atoms.

[3] A method for producing a fluorine-containing pyrimidine compound, including
(a) reacting a fluoroisobutylene derivative represented by the following formula (3) with a compound represented by the following formula (4) or a salt thereof to obtain a fluorine-containing pyrimidine compound represented by the following formula (1), or

[Formula 2]

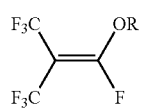
(3)

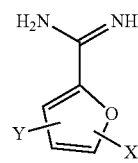
(4)

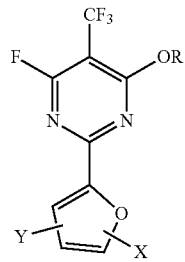
(1)

(b) reacting a fluoroisobutylene derivative represented by the following formula (3) with a compound represented by the following formula (5) or a salt thereof to obtain a fluorine-containing pyrimidine compound represented by the following formula (2):

[Formula 3]

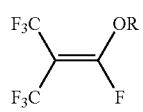
(3)

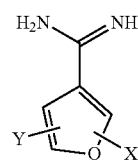
(5)

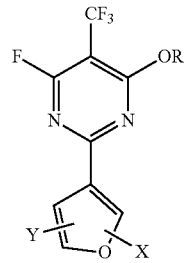
(2)

wherein in the formulae (1) to (5) above,
R represents a hydrocarbon group having 1 to 12 carbon atoms; and
X and Y each independently represent a hydrogen atom, a halogen atom, a hydrocarbon group having 1 to 10 carbon atoms, —$C_nF_{2n+1}$ where n is an integer of 1 to 10, a nitro group, a boronic acid group, —$OA^1$, —$SO_mA^1$ where m is an integer of 0 to 3, —$NA^1A^2$, —$COOA^1$, or —$CONA^1A^2$, where $A^1$ and $A^2$ each independently represent a hydrogen atom or a hydrocarbon group having 1 to 10 carbon atoms.

[4] A method for producing a fluorine-containing pyrimidine compound, including
(c) reacting a fluoroisobutane derivative represented by the following formula (6) with a compound represented by the following formula (4) or a salt thereof to obtain a fluorine-containing pyrimidine compound represented by the following formula (1), or

[Formula 4]

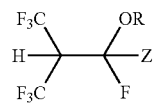
(6)

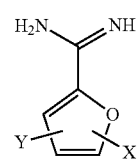
(4)

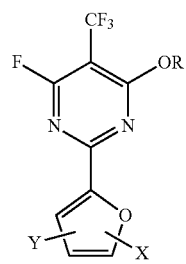
(1)

(d) reacting a fluoroisobutane derivative represented by the following formula (6) with a compound represented by the following formula (5) or a salt thereof to obtain a fluorine-containing pyrimidine compound represented by the following formula (2):

[Formula 5]

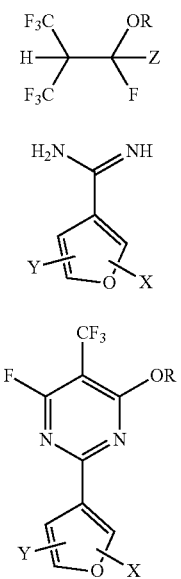

(6)

(5)

(2)

wherein in the formulae (1) and (2), and (4) to (6) above,

R represents a hydrocarbon group having 1 to 12 carbon atoms; and

X and Y each independently represent a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$, or $-CONA^1A^2$, and Z represents a halogen atom, $-OA^1$, $-SO_mA^1$ where m is an integer of 0 to 3, or $-NA^1A^2$, where $A^1$ and $A^2$ each independently represent a hydrogen atom or a hydrocarbon group having 1 to 10 carbon atoms.

[5] The method for producing a fluorine-containing pyrimidine compound according to [3], wherein R is an alkyl group having 1 to 10 carbon atoms.

[6] The method for producing a fluorine-containing pyrimidine compound according to [4], wherein R is an alkyl group having 1 to 10 carbon atoms.

Effects of Disclosure

A novel fluorine-containing pyrimidine compound having substituents at the 4-, 5-, and 6-positions and a furan ring structure as a substituent at the 2-position, and a method capable of easily producing the fluorine-containing pyrimidine compound, can be provided.

DETAILED DESCRIPTION

Fluorine-Containing Pyrimidine Compound

The fluorine-containing pyrimidine compound according to an embodiment is represented by the following formula (1) or (2):

[Formula 6]

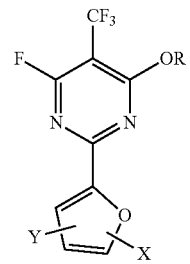

(1)

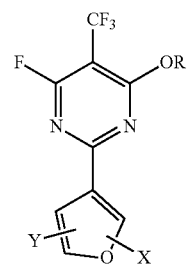

(2)

wherein in formulae (1) and (2) above,

R represents a hydrocarbon group having 1 to 12 carbon atoms; and

X and Y each independently represent a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$, or $-CONA^1A^2$, where $A^1$ and $A^2$ each independently represent a hydrogen atom or a hydrocarbon group having 1 to 10 carbon atoms. In one embodiment of the fluorine-containing pyrimidine compound, a furyl group having a single ring or a condensed heterocyclic group containing a furan ring as a part thereof may be present as a substituent at the 2-position of a pyrimidine ring.

R is not particularly limited as long as it is a hydrocarbon group having 1 to 12 carbon atoms and is composed of a carbon atom and a hydrogen atom, and includes a chain hydrocarbon group, an aromatic hydrocarbon group, an alicyclic hydrocarbon group and the like. The chain hydrocarbon group is not particularly limited as long as the total number of carbon atoms is 1 to 12 and may be a branched chain hydrocarbon group or a chain hydrocarbon group having no branch. The aromatic hydrocarbon group is not particularly limited as long as the total number of carbon atoms is 5 to 12 and may even be an aromatic hydrocarbon group having a substituent or an aromatic hydrocarbon group having no substituent. Moreover, the aromatic hydrocarbon group may have a condensed polycyclic structure. The alicyclic hydrocarbon group is not particularly limited as long as the total number of carbon atoms is 3 to 12 and may even be an alicyclic hydrocarbon group having a substituent or an alicyclic hydrocarbon group having no substituent. Further, the alicyclic hydrocarbon group may have a bridged ring structure.

Examples of the chain hydrocarbon group include alkyl groups such as a methyl group, an ethyl group, an n-propyl group, an i-propyl group, a n-butyl group, an i-butyl group, a sec-butyl group, a t-butyl group, a pentyl group, a hexyl group, a heptyl group, an octyl group, a nonyl group, a decyl group, an undecyl group, a dodecyl group;

alkenyl groups such as an ethenyl group, a propenyl group, a butenyl group, a pentenyl group, a hexenyl group, a heptenyl group, an octenyl group, a nonenyl group, a decenyl group, an undecenyl group, a dodecenyl group; and alkynyl groups such as an ethynyl group, a propynyl group, a butynyl group, a pentynyl group, a hexynyl group, a heptynyl group, an octynyl group, a nonynyl group, a decynyl group, an undecynyl group, a dodecynyl group.

Examples of the aromatic hydrocarbon group include a phenyl group and a naphthyl group.

Examples of the alicyclic hydrocarbon group include a saturated or unsaturated cyclic hydrocarbon group, and examples of the cyclic hydrocarbon group include a cyclopropyl group, a cyclobutyl group, a cyclohexyl group, a cyclopentyl group, an adamantyl group, a norbornyl group and the like.

R is preferably an alkyl group having 1 to 10 carbon atoms. R being an alkyl group having 1 to 10 carbon atoms can easily prepare the fluoroisobutylene derivative of the general formula (3) and the fluoroisobutane derivative of the general formula (6), which are raw materials of the fluorine-containing pyrimidine compound.

Examples of the halogen atoms that are X and Y include F, Cl, Br, and I. $A^1$ included in —$OA^1$ and —$SO_mA^1$ where m is an integer of 0 to 3, which is X or Y, represents a hydrogen atom or a hydrocarbon group having 1 to 10 carbon atoms. $A^1$ and $A^2$ included in —$NA^1A^2$, which are X and Y, each independently represent a hydrogen atom or a hydrocarbon group having 1 to 10 carbons. $A^1$ and $A^2$ each representing a hydrocarbon group having 1 to 10 carbon atoms, can be, for example, a hydrocarbon group having 1 to 10 carbon atoms in R above. More specifically, —$SO_mA^1$ can be a methane sulfonyl group.

$A^1$ included in —$COOA^1$, which is X or Y, is a hydrogen atom or a hydrocarbon group having 1 to 10 carbon atoms, and it can be, for example, a hydrocarbon group having 1 to 10 carbon atoms in R above. More specifically, —$COOA^1$ can be a methoxycarbonyl group.

$A^1$ and $A^2$ included in —$CONA^1A^2$, which are X and Y, each independently represent a hydrogen atom or a hydrocarbon group having 1 to 10 carbon atoms. $A^1$ and $A^2$ each representing a hydrocarbon group having 1 to 10 carbons, can be, for example, a hydrocarbon group having 1 to 10 carbon atoms in R above. X and Y are preferably hydrogen atoms.

In the general formulae (1) and (2), when X and Y present as substituents on a furan ring structure are adjacent, X and Y may bind to each other to form a ring together with the carbon atoms to which they bind. When X and Y bind to form a ring, examples of the fluorine-containing pyrimidine compound include a fluorine-containing pyrimidine compound in which a condensed heterocyclic group containing an oxygen atom exists as a substituent at the 2-position of the pyrimidine ring. In this case, the benzofuranyl group can be exemplified as the substituent present at the 2-position of the pyrimidine ring.

The fluorine-containing pyrimidine compound according to an embodiment has a specific substituent (furyl group or condensed heterocyclic group containing a furan ring as a part thereof) at the 2-position of the pyrimidine ring and specific substituents (—OR, —$CF_3$, —F) at the 4-, 5-, and 6-positions of the pyrimidine ring, and therefore can have an excellent effect from the viewpoint of structural extensibility. In particular, desirable biological activity (for example, hormone or enzyme inhibitory activity, bactericidal activity, insecticidal activity, herbicidal activity) can be expected. The furan ring structure located at the 2-position of the pyrimidine ring is present as a 2-furyl group or a 3-furyl group or a condensed heterocyclic group containing a furan ring as a part thereof, and the furan ring structure may have an additional substituent or no substituent. The presence of the substituent on the furan ring structure can impart additional properties to the fluorine-containing pyrimidine compound of one embodiment. Moreover, the substituents at the 4- and 6-positions of the pyrimidine ring being different groups (—OR and —F) facilitates derivatization into an asymmetric structure, which can be expected to be used as an intermediate. More specifically, the fluorine-containing pyrimidine compound being reacted under acidic conditions to modify —OR enables to form a derivative. Further, the fluorine-containing pyrimidine compound being reacted under basic conditions to modify —F enables to form a derivative. The fluorine-containing pyrimidine compound of one embodiment is useful in the field of, for example, electronic materials such as organic semiconductors and liquid crystals.

Method for Producing Fluorine-Containing Pyrimidine Compound

The method for producing a fluorine-containing pyrimidine compound in one embodiment includes (a) reacting a fluoroisobutylene derivative represented by the following formula (3) with a compound represented by the following formula (4) or a salt thereof to obtain a fluorine-containing pyrimidine compound represented by the following formula (1), or

[Formula 7]

(3)

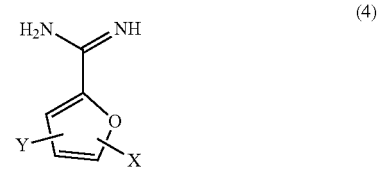

(4)

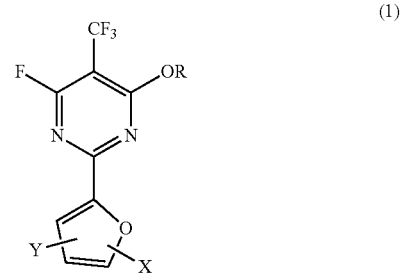

(1)

(b) reacting a fluoroisobutylene derivative represented by the following formula (3) with a compound represented by the following formula (5) or a salt thereof to obtain a fluorine-containing pyrimidine compound represented by the following formula (2):

[Formula 8]

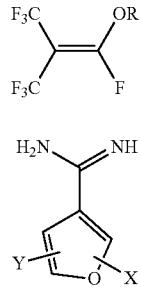
(3)

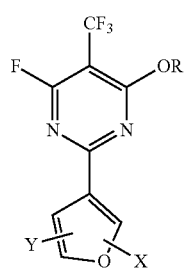
(5)

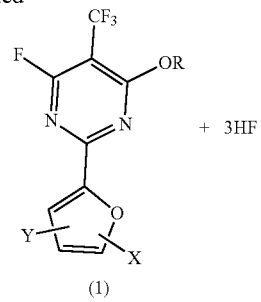
(1)

(2)

The reaction of fluoroisobutylene derivative represented by the general formula (3) with the compound represented by the general formula (5) in (b) above is represented by the following reaction formula (B).

[Formula 10]

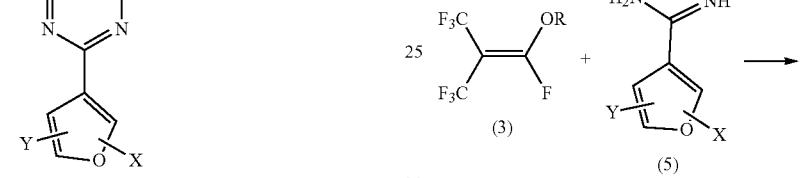
(B)

wherein in formulae (1) to (5) above,

R represents a hydrocarbon group having 1 to 12 carbon atoms; and

X and Y each independently represent a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$, or $-CONA^1A^2$, where $A^1$ and $A^2$ each independently represent a hydrogen atom or a hydrocarbon group having 1 to 10 carbon atoms.

R in formulae (1) to (3) above preferably represents an alkyl group having 1 to 10 carbon atoms. As described above, in the general formulae (1), (2), (4) and (5) of steps (a) and (b), when X and Y are adjacent, X and Y may bind to each other to form a ring together with the carbon atoms to which they bind.

The reaction of fluoroisobutylene derivative represented by the general formula (3) with the compound represented by the general formula (4) in (a) above is represented by the following reaction formula (A).

[Formula 9]

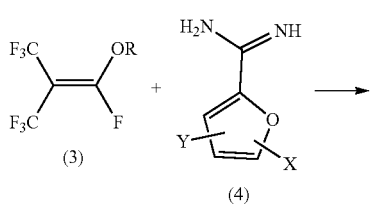
(A)

In the reaction formulae (A) and (B) above, the compounds of the general formulae (4) and (5) each may be in a form of salt. The form of salt includes, for example, a form of at least one of the amino moiety ($-NH_2^+$) and the imino moiety ($=NH$) constituting the amidino group of the compound of the general formulae (4) and (5), being cationized to ($-NH_3^+$) and ($=NH_2^+$) to form a salt with the counterion. The counterion is not particularly limited as long as it is a monovalent anion, and includes, for example, halide ions such as $F^-$, $Cl^-$, $Br^-$, and $I^-$.

In the method for producing the fluorine-containing pyrimidine compound in one embodiment, for example, reaction (a) and (b) above can be carried out in one step in the presence of the hydrogen halide scavenger. Therefore, the fluorine-containing pyrimidine compounds of formulae (1) and (2) above can be easily obtained. Incidentally, the reaction of (a) and (b) above forms a cyclic pyrimidine structure between the fluoroisobutylene derivative and the amidino group of the compounds of the general formulae (4) and (5). At the 2-position of the pyrimidine structure, a group derived from the furan ring structure of the compounds of the general formulae (4) and (5) is located. Moreover, $-OR$, $CF_3$, and F derived from fluoroisobutylene derivatives are located at the 4-, 5-, and 6 positions of the pyrimidine structure, respectively.

The hydrogen halide scavenger is a substance having a function of capturing hydrogen fluoride (HF) formed from a hydrogen atom derived from the amidino group in the compounds of the general formulae (4) and (5) in reaction formulae (A) and (B) above, and a fluorine atom derived from the fluoroisobutylene derivative of formula (3). The hydrogen halide scavenger that is sodium hydroxide, potassium hydroxide, calcium hydroxide, sodium carbonate, potassium carbonate, sodium fluoride and potassium fluoride, and organic nitrogen derivatives such as pyridine, triethylamine, diisopropylethylamine, diazabicyclo nonane and diazabicyclo undecene, methyl triazabicyclodecene, and diazabicyclo octane, can be used.

A reaction temperature upon reaction of (a) and (b) above is preferably 0 to 80° C., more preferably 5 to 50° C., and still more preferably 10 to 25° C. A reaction time upon the reactions of (a) and (b) above is preferably 8 to 72 hours, more preferably 12 to 48 hours, and still more preferably 16 to 36 hours.

A solvent used in reaction (a) and (b) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water, and a water-insoluble solvent such as dichloromethane, toluene and diethyl ether. Moreover, as a catalyst for reaction of (a) and (b) above, quaternary ammonium halides such as benzyltriethylammonium chloride, a quaternary phosphonium halide, and crown ether, can be used.

The method for producing a fluorine-containing pyrimidine compound of another embodiment includes (c) reacting a fluoroisobutane derivative represented by the following formula (6) with a compound represented by the following formula (4) or a salt thereof to obtain a fluorine-containing pyrimidine compound represented by the following formula (1), or

[Formula 11]

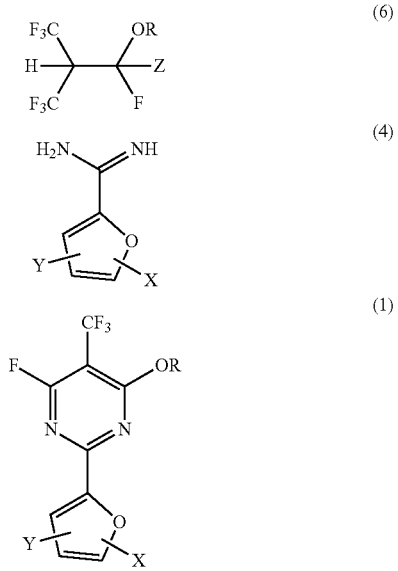

(d) reacting a fluoroisobutane derivative represented by the following formula (6) with a compound represented by the following formula (5) or a salt thereof to obtain a fluorine-containing pyrimidine compound represented by the following formula (2):

[Formula 12]

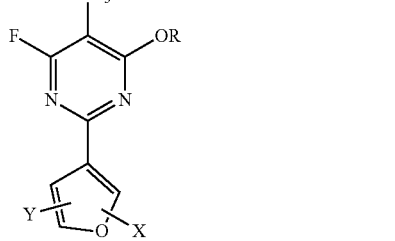

wherein in formulae (1) and (2), and (4) to (6) above,
represents a hydrocarbon group having 1 to 12 carbon atoms;
X and Y each independently represent a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$, or $-CONA^1A^2$, and Z represents a halogen atom, $-OA^1$, $-SO_mA^1$ where m is an integer of 0 to 3, or $-NA^1A^2$, where $A^1$ and $A^2$ each independently represent a hydrogen atom or a hydrocarbon group having 1 to 10 carbon atoms.

$A^1$ and $A^2$ in the compounds of the general formulae (1) and (2), and (4) to (6) in steps (c) and (d) above can be specifically the same as $A^1$ and $A^2$, respectively, in the compounds of the general formulae (1) and (2) in steps (a) and (b) above.

R in the general formulae (1), (2) and (6) above preferably represents an alkyl group having 1 to 10 carbon atoms. As described above, in the general formulae (1), (2), (4) and (5) of steps (c) and (d), when X and Y are adjacent, X and Y may bind to each other to form a ring together with the carbon atoms to which they bind.

The reaction of the fluoroisobutane derivative represented by the general formula (6) with the compound represented by the general formula (4) in (c) above is represented by the following reaction formula (C).

[Formula 13]

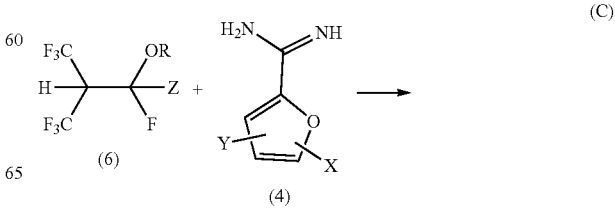

-continued

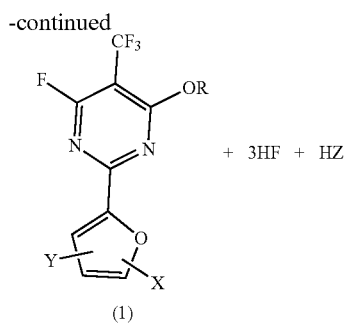

+ 3HF + HZ (1)

The reaction of the fluoroisobutane derivative represented by the general formula (6) with the compound represented by the general formula (5) in (d) above is represented by the following reaction formula (D).

[Formula 14]

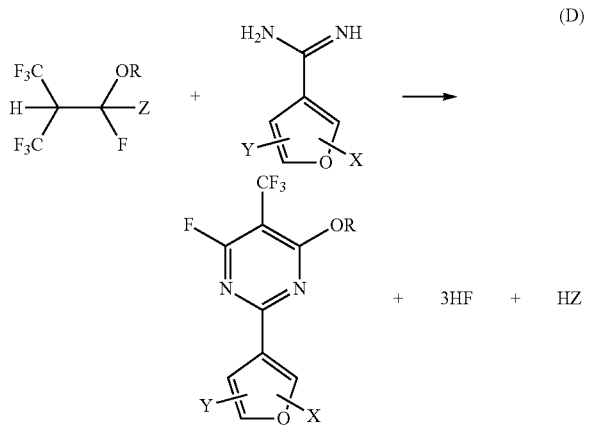

+ 3HF + HZ (D)

In reaction formulae (C) and (D) above, the compounds of formulae (4) and (5) may be in the form of salts, respectively. The form of salt includes, for example, a form of at least one of the amino moiety (—$NH_2$) and the imino moiety (=NH) constituting the amidino group of the compounds of formulae (4) and (5), being cationized to (—$NH_3^+$) and (=$NH_2^+$) to form a salt with the counterion. The counterion is not particularly limited as long as it is a monovalent anion, and includes, for example, halide ions such as $F^-$, $Cl^-$, $Br^-$, and $I^-$.

In the method for producing the fluorine-containing pyrimidine compound in the other embodiment, for example, the reaction of (C) and (D) above can be carried out in one step. Therefore, the fluorine-containing pyrimidine compounds of the general formulae (1) and (2) above can be easily obtained. The reaction of (c) and (d) above form a cyclic pyrimidine structure between the fluoroisobutane derivative and the amidino group of the compounds of the general formulae (4) and (5). At the 2-position of the pyrimidine structure, a group derived from the furan ring structure of the compounds of the general formulae (4) and (5) is located. Further, —OR, $CF_3$, and F derived from the fluoroisobutane derivatives are located at the 4-, 5-, and 6-positions of the pyrimidine structure, respectively.

A reaction temperature upon reaction of (c) and (d) above is preferably 0 to 80° C., more preferably 5 to 50° C., and still more preferably 10 to 25° C. A reaction time upon reactions of (c) and (d) above is preferably 8 to 72 hours, more preferably 12 to 48 hours, and still more preferably 16 to 36 hours. In the reactions of (c) and (d) above, the same hydrogen halide scavenger as in (a) and (b) above can be used.

A solvent used in reaction (c) and (d) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water and a water-insoluble solvent such as dichloromethane, toluene and diethyl ether. Moreover, as a catalyst for reaction (c) and (d) above, quaternary ammonium halides such as benzyltriethylammonium chloride, a quaternary phosphonium halide, crown ether and the like, can be used.

Although the embodiments of the present disclosure have been described above, the present disclosure is not limited to the aforementioned embodiments, and includes all aspects included in the concept and claims of the present disclosure and can be modified within the scope of the present disclosure.

EXAMPLES

Next, in order to further clarify the effect of the present disclosure, Examples will be described, but the present disclosure is not limited to these Examples.

Example 1

Production of 6-fluoro-4-methoxy-2-(2-furanyl)-5-trifluoromethylpyrimidine

Under ice-water cooling, 25 g (0.15 mol) of 2-amidinofuran hydrochloride and 25 g (0.12 mol) of 1,3,3,3-tetrafluoro-1-methoxy-2-trifluoromethyl-1-propene were added to 75 g of dichloromethane and 75 g of water. Subsequently, 120 ml (0.60 mol) of 5N sodium hydroxide aqueous solution (hydrogen halide scavenger) was added dropwise such that the internal temperature did not exceed 10° C., and the mixture was raised to room temperature. After stirring for about 16 hours, the organic phase was separated. After removal of dichloromethane from the organic phase under reduced pressure, column purification of the solution dissolved in ethyl acetate was performed to obtain 4.6 g of a target product (6-fluoro-4-methoxy-2-(2-furanyl)-5-trifluoromethylpyrimidine) represented by the following formula (E). The isolated yield of 6-fluoro-4-methoxy-2-(2-furanyl)-5-trifluoromethylpyrimidine was 14%.

[Formula 15]

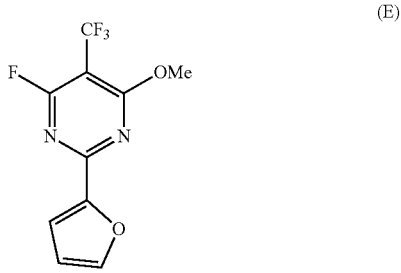

(E)

The analysis results of the target product obtained are as follows.

Mass Spectrum (APCI, m/z): 262 ([M]$^+$)

$^1$H-NMR (300 MHz, CDCl$_3$) δ ppm: 7.68 (s, 1H), 7.45 (d, 1H), 7.26 (s, 1H), 4.20 (s, 3H)

$^{19}$F-NMR (300 MHz, C$_6$F$_6$) δ ppm: −58.44 (d, 3F), −61.22 (dd, 1F)

Example 2

Production of 6-fluoro-4-methoxy-2-(3-furanyl)-5-trifluoromethylpyrimidine

Under ice-water cooling, 10 g (61 mmol) of 3-amidinofuran hydrochloride and 11 g (55 mmol) of 1,3,3,3-tetrafluoro-1-methoxy-2-trifluoromethyl-1-propene were added to 75 g of dichloromethane and 75 g of water. Subsequently, 48 ml (0.24 mol) of 5N sodium hydroxide aqueous solution (hydrogen halide scavenger) was added dropwise such that the internal temperature did not exceed 10° C., and the mixture was raised to room temperature. After stirring for about 16 hours, the organic phase was separated. After removal of dichloromethane from the organic phase under reduced pressure, column purification of the solution dissolved in ethyl acetate was performed to obtain 2.0 g of a target product (6-fluoro-4-methoxy-2-(3-furanyl)-5-trifluoromethylpyrimidine) represented by the following formula (F). The isolated yield of 6-fluoro-4-methoxy-2-(3-furanyl)-5-trifluoromethylpyrimidine was 14%.

[Formula 16]

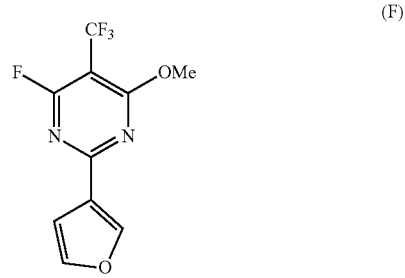

(F)

The analysis results of the target product obtained are as follows.

Mass Spectrum (APCI, m/z): 262 ([M]$^+$)

$^1$H-NMR (300 MHz, CDCl$_3$) δ ppm: 8.29 (s, 1H), 7.50 (s, 1H), 7.01 (d, 1H), 4.17 (s, 3H)

$^{19}$F-NMR (300 MHz, C$_6$F$_6$) δ ppm: −58.43 (d, 3F), −62.14 (dd, 1F)

Example 3

Production of 6-fluoro-4-methoxy-2-(2-furanyl)-5-trifluoromethylpyrimidine by Using 1,1,1,3,3-pentafluoro-3-methoxy-2-trifluoromethyl-propane Instead of 1,3,3,3-tetrafluoro-1-methoxy-2-trifluoromethyl-1-propene of Example 1

Under ice-water cooling, 25 g (0.15 mol) of 2-amidinofuran hydrochloride and 28 g (0.12 mol) of 1,1,1,3,3-pentafluoro-3-methoxy-2-trifluoromethyl-propane were added to 75 g of dichloromethane and 75 g of water. Subsequently, 150 ml (0.75 mol) of 5N sodium hydroxide aqueous solution (hydrogen halide scavenger) was added dropwise such that the internal temperature did not exceed 10° C., and the mixture was raised to room temperature. After stirring for about 16 hours, the organic phase was separated. After removal of dichloromethane from the organic phase under reduced pressure, column purification of the solution dissolved in ethyl acetate was performed. The analysis results of the obtained compound were the same as those of the product of Example 1.

Example 4

Production of 6-fluoro-4-methoxy-2-(3-furanyl)-5-trifluoromethylpyrimidine by Using 1,1,1,3,3-pentafluoro-3-methoxy-2-trifluoromethyl-propane Instead of 1,3,3,3-tetrafluoro-1-methoxy-2-trifluoromethyl-1-propene of Example 2

Under ice-water cooling, 10 g (61 mmol) of 3-amidinofuran hydrochloride and 13 g (55 mmol) of 1,1,1,3,3-pentafluoro-3-methoxy-2-trifluoromethyl-propane were added to 75 g of dichloromethane and 75 g of water. Subsequently, 62 ml (0.31 mol) of 5N sodium hydroxide aqueous solution (hydrogen halide scavenger) was added dropwise such that the internal temperature did not exceed 10° C., and the mixture was raised to room temperature. After stirring for about 16 hours, the organic phase was separated. After removal of dichloromethane from the organic phase under reduced pressure, column purification of the solution dissolved in ethyl acetate was performed. The analysis results of the obtained compound were the same as those of the product of Example 2.

Example 5

Production of 6-fluoro-4-methoxy-2-(5-chloro-2-furanyl)-5-trifluoromethylpyrimidine 0.7 g (3.8 mmol) of 5-chlorofuran-2-carboxyimideamide hydrochloride was dissolved in 38 ml of acetonitrile to prepare an acetonitrile solution. 0.9 g (4.2 mmol) of 1,3,3,3-tetrafluoro-1-methoxy-2-trifluoromethyl-1-propene and 2.6 g (20.1 mmol) of N,N-diisopropyl ethylamine were added to the acetonitrile solution, and the mixture was stirred for 16.5 hours at room temperature to obtain 6-fluoro-4-methoxy-2-(5-chloro-2-furanyl)-5-trifluoromethylpyrimidine from 5-chlorofuran-2-carboxyimideamide hydrochloride according to a formula represented by the following formula (G). After that, column purification of a solution after reaction was performed to obtain 0.8 g (2.7 mmol) of a target product (6-fluoro-4-methoxy-2-(5-chloro-2-furanyl)-5-trifluoromethylpyrimidine). The isolated yield of 6-fluoro-4-methoxy-2-(5-chloro-2-furanyl)-5-trifluoromethylpyrimidine was 72.1%.

[Formula 17]

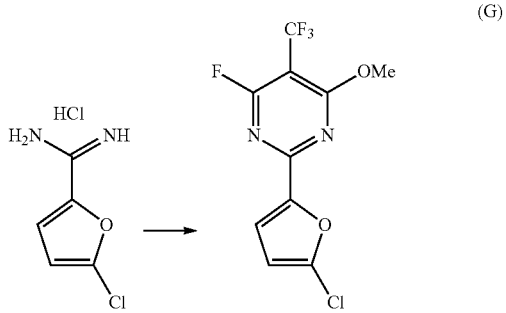

(G)

The analysis results of the target product obtained are as follows.

Mass Spectrum (APClMS, m/z): 296.0 [M+H]+

1H-NMR (400 MHz, CDCl3) δ 7.42 (d, J=3.7 Hz, 1H), 6.41 (d, J=3.4 Hz, 1H), 4.19 (s, 3H)

Example 6

Production of 6-fluoro-4-methoxy-2-(5-bromo-2-furanyl)-5-trifluoromethylpyrimidine 0.6 g (2.7 mmol) of 5-bromofuran-2-carboxyimideamide hydrochloride was dissolved in 27 ml of acetonitrile to prepare an acetonitrile solution. 0.7 g (3.3 mmol) of 1,3,3,3-tetrafluoro-1-methoxy-2-trifluoromethyl-1-propene and 1.8 g (13.9 mmol) of N,N-diisopropyl ethylamine were added to the acetonitrile solution, and the mixture was stirred for 20.7 hours at room temperature to obtain 6-fluoro-4-methoxy-2-(5-bromo-2-furanyl)-5-trifluoromethylpyrimidine from 5-bromofuran-2-carboxyimideamide hydrochloride according to a formula represented by the following formula (H). After that, column purification of a solution after reaction was performed to obtain 0.7 g (2.0 mmol) of a target product (6-fluoro-4-methoxy-2-(5-bromo-2-furanyl)-5-trifluoromethylpyrimidine). The isolated yield of 6-fluoro-4-methoxy-2-(5-bromo-2-furanyl)-5-trifluoromethylpyrimidine was 75.3%.

[Formula 18]

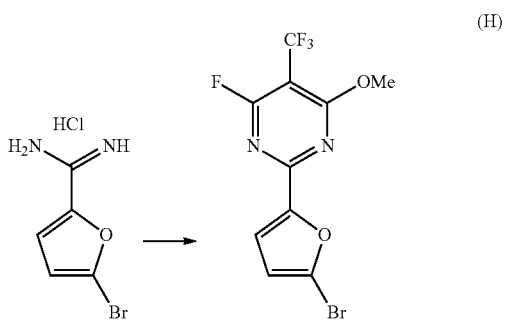

(H)

The analysis results of the target product obtained are as follows.

Mass Spectrum (APClMS, m/z): 339.9 [M+H]+

1H-NMR (400 MHz, CDCl3) δ 7.39 (d, J=3.4 Hz, 1H), 6.55 (d, J=3.7 Hz, 1H), 4.19 (s, 3H)

Example 7

Production of 6-fluoro-4-methoxy-2-(2-methyl-3-furanyl)-5-trifluoromethylpyrimidine 0.3 g (1.8 mmol) of 2-methylfuran-3-carboxyimideamide hydrochloride was dissolved in 18 ml of acetonitrile to prepare an acetonitrile solution. 0.4 g (1.9 mmol) of 1,3,3,3-tetrafluoro-1-methoxy-2-trifluoromethyl-1-propene and 1.2 g (9.3 mmol) of N,N-diisopropyl ethylamine were added to the acetonitrile solution, and the mixture was stirred for 23.7 hours at room temperature to obtain 6-fluoro-4-methoxy-2-(2-methyl-3-furanyl)-5-trifluoromethylpyrimidine from 2-methylfuran-3-carboxyimideamide hydrochloride according to a formula represented by the following formula (I). After that, column purification of a solution after reaction was performed to obtain 0.02 g (0.05 mmol) of a target product (6-fluoro-4-methoxy-2-(2-methyl-3-furanyl)-5-trifluoromethylpyrimidine). The isolated yield of 6-fluoro-4-methoxy-2-(2-methyl-3-furanyl)-5-trifluoromethylpyrimidine was 3.0%.

[Formula 19]

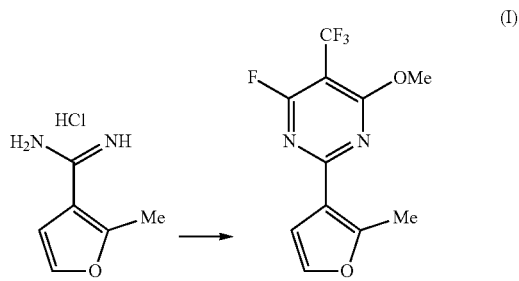

(I)

The analysis results of the target product obtained are as follows.

Mass Spectrum (APClMS, m/z): 277.0 [M+H]+

1H-NMR (400 MHz, CDCl3) δ 7.32 (d, J=2.1 Hz, 1H), 6.97 (d, J=4.1 Hz, 1H), 4.16 (s, 3H), 2.77 (s, 3H)

Example 8

Production of 6-fluoro-4-methoxy-2-(5-nitro-2-furanyl)-5-trifluoromethylpyrimidine 0.6 g (3.2 mmol) of 5-nitrofuran-2-carboxyimideamide hydrochloride was dissolved in 34 ml of acetonitrile to prepare an acetonitrile solution. 0.8 g (3.8 mmol) of 1,3,3,3-tetrafluoro-1-methoxy-2-trifluoromethyl-1-propene and 2.3 g (17.8 mmol) of N,N-diisopropyl ethylamine were added to the acetonitrile solution, and the mixture was stirred for 23.8 hours at room temperature to obtain 6-fluoro-4-methoxy-2-(5-nitro-2-furanyl)-5-trifluoromethylpyrimidine from 5-nitrofuran-2-carboxyimideamide hydrochloride according to a formula represented by the following formula (J). After that, column purification of a solution after reaction was performed to obtain 0.4 g (1.1 mmol) of a target product (6-fluoro-4-methoxy-2-(5-nitro-2-furanyl)-5-trifluoromethylpyrimidine). The isolated yield of 6-fluoro-4-methoxy-2-(5-nitro-2-furanyl)-5-trifluoromethylpyrimidine was 34.1%.

[Formula 20]

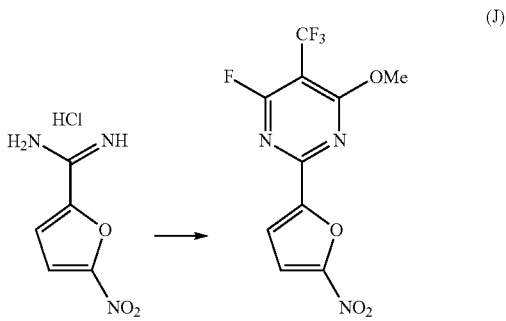

(J)

The analysis results of the target product obtained are as follows.

Mass Spectrum (APCIMS, m/z): 306.8 [M–H]+
¹H-NMR (400 MHz, CDCl₃) δ 7.54 (d, J=3.7 Hz, 1H), 7.44 (d, J=4.0 Hz, 1H), 4.26 (s, 3H)

Example 9

Production of 6-fluoro-4-methoxy-2-(5-methansulfonyl-2-furanyl)-5-trifluoromethylpyrimidine 0.5 g (2.3 mmol) of 5-methansulfonylfuran-2-carboxyimideamide hydrochloride was dissolved in 23 ml of acetonitrile to prepare an acetonitrile solution. 0.6 g (2.8 mmol) of 1,3,3,3-tetrafluoro-1-methoxy-2-trifluoromethyl-1-propene and 1.5 g (11.6 mmol) of N,N-diisopropyl ethylamine were added to the acetonitrile solution, and the mixture was stirred for 23.5 hours at room temperature to obtain 6-fluoro-4-methoxy-2-(5-methansulfonyl-2-furanyl)-5-trifluoromethylpyrimidine from 5-methansulfonylfuran-2-carboxyimideamide hydrochloride according to a formula represented by the following formula (K). After that, column purification of a solution after reaction was performed to obtain 0.4 g (1.2 mmol) of a target product (6-fluoro-4-methoxy-2-(5-methansulfonyl-2-furanyl)-5-trifluoromethylpyrimidine). The isolated yield of 6-fluoro-4-methoxy-2-(5-methansulfonyl-2-furanyl)-5-trifluoromethylpyrimidine was 50.9%.

[Formula 21]

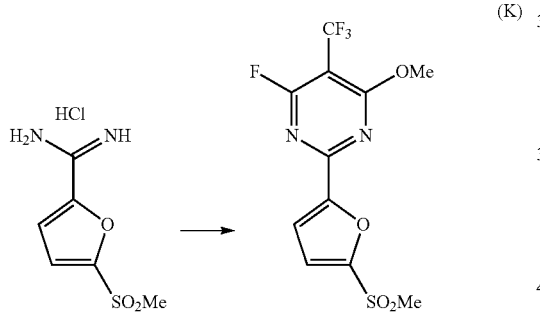

(K)

The analysis results of the target product obtained are as follows.
Mass Spectrum (APCIMS, m/z): 341.2 [M+H]+
¹H-NMR (400 MHz, CDCl₃) δ 7.49 (d, J=3.7 Hz, 1H), 7.31 (d, J=3.7 Hz, 1H), 4.23 (s, 3H), 3.27 (s, 3H)

Example 10

Production of 6-fluoro-4-methoxy-2-(2-methoxycarbonyl-4-furanyl)-5-trifluoromethylpyrimidine 0.6 g (3.0 mmol) of 5-carbamimidoylfuran-2-methyl carboxylate hydrochloride was dissolved in 30 ml of acetonitrile to prepare an acetonitrile solution. 0.7 g (3.3 mmol) of 1,3,3,3-tetrafluoro-1-methoxy-2-trifluoromethyl-1-propene and 2.0 g (15.5 mmol) of N,N-diisopropyl ethylamine were added to the acetonitrile solution, and the mixture was stirred for 16 hours at room temperature to obtain 6-fluoro-4-methoxy-2-(2-methoxycarbonyl-4-furanyl)-5-trifluoromethylpyrimidine from 5-carbamimidoylfuran-2-methyl carboxylate hydrochloride according to a formula represented by the following formula (L). After that, column purification of a solution after reaction was performed to obtain 0.2 g (0.5 mmol) of a target product (6-fluoro-4-methoxy-2-(2-methoxycarbonyl-4-furanyl)-5-trifluoromethylpyrimidine). The isolated yield of 6-fluoro-4-methoxy-2-(2-methoxycarbonyl-4-furanyl)-5-trifluoromethylpyrimidine was 16.2%.

[Formula 22]

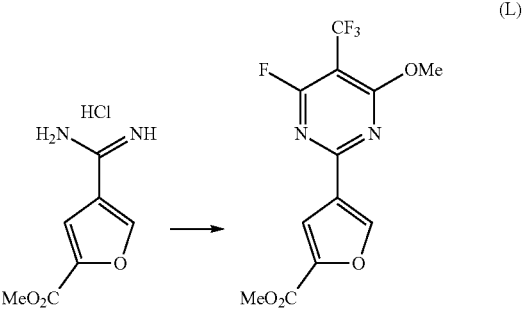

(L)

The analysis results of the target product obtained are as follows.
Mass Spectrum (APCIMS, m/z): 321.5 [M+H]+
¹H-NMR (400 MHz, CDCl₃) δ 8.38 (d, J=1.0 Hz, 1H), 7.76 (d, J=0.8 Hz, 1H), 4.19 (s, 3H), 3.95 (s, 3H)

Example 11

Production of 6-fluoro-4-methoxy-2-(5-iodo-2-furanyl)-5-trifluoromethylpyrimidine 0.5 g (1.9 mmol) of 5-iodofuran-2-carboxyimideamide hydrochloride was dissolved in 26 ml of acetonitrile to prepare an acetonitrile solution. 0.6 g (2.8 mmol) of 1,3,3,3-tetrafluoro-1-methoxy-2-trifluoromethyl-1-propene and 1.7 g (13.2 mmol) of N,N-diisopropyl ethylamine were added to the acetonitrile solution, and the mixture was stirred for 16.7 hours at room temperature to obtain 6-fluoro-4-methoxy-2-(5-iodo-2-furanyl)-5-trifluoromethylpyrimidine from 5-iodofuran-2-carboxyimideamide hydrochloride according to a formula represented by the following formula (M). After that, column purification of a solution after reaction was performed to obtain 0.5 g (1.2 mmol) of a target product (6-fluoro-4-methoxy-2-(5-iodo-2-furanyl)-5-trifluoromethylpyrimidine). The isolated yield of 6-fluoro-4-methoxy-2-(5-iodo-2-furanyl)-5-trifluoromethylpyrimidine was 66.3%.

[Formula 23]

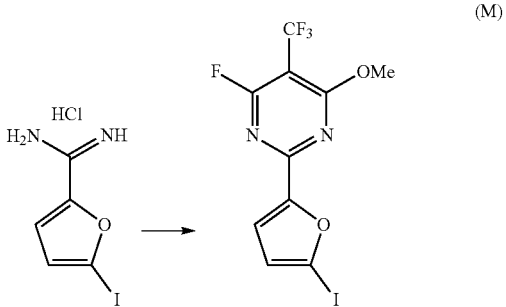

(M)

The analysis results of the target product obtained are as follows.
Mass Spectrum (APCIMS, m/z): 387.6 [M+H]+
¹H-NMR (400 MHz, CDCl₃) δ 7.32 (d, J=3.7 Hz, 1H), 6.78 (d, J=3.4 Hz, 1H), 4.19 (s, 3H)

The invention claimed is:

1. A fluorine-containing pyrimidine compound represented by the following formula (1) or (2):

[Formula 1]

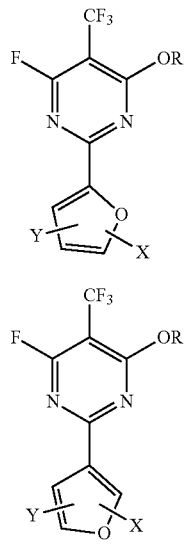

wherein

R represents a hydrocarbon group having 1 to 12 carbon atoms; and

X and Y each independently represent a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$, or $-CONA^1A^2$, where $A^1$ and $A^2$ each independently represent a hydrogen atom or a hydrocarbon group having 1 to 10 carbon atoms.

2. The fluorine-containing pyrimidine compound according to claim 1, wherein R is an alkyl group having 1 to 10 carbon atoms.

3. A method for producing a fluorine-containing pyrimidine compound, comprising (a) reacting a fluoroisobutylene derivative represented by the following formula (3) with a compound represented by the following formula (4) or a salt thereof to obtain a fluorine-containing pyrimidine compound represented by the following formula (1), or

[Formula 2]

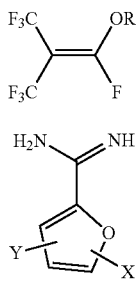

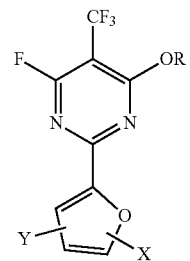

(b) reacting a fluoroisobutylene derivative represented by the following formula (3) with a compound represented by the following formula (5) or a salt thereof to obtain a fluorine-containing pyrimidine compound represented by the following formula (2):

[Formula 3]

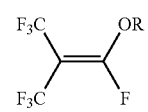

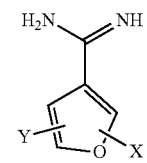

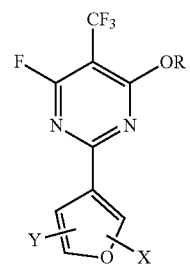

wherein in the formulae (1) to (5) above,

R represents a hydrocarbon group having 1 to 12 carbon atoms; and

X and Y each independently represent a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$, or $-CONA^1A^2$, where $A^1$ and $A^2$ each independently represent a hydrogen atom or a hydrocarbon group having 1 to 10 carbon atoms.

4. A method for producing a fluorine-containing pyrimidine compound, comprising (c) reacting a fluoroisobutane derivative represented by the following formula (6) with a compound represented by the following formula (4) or a salt thereof to obtain a fluorine-containing pyrimidine compound represented by the following formula (1), or

[Formula 4]

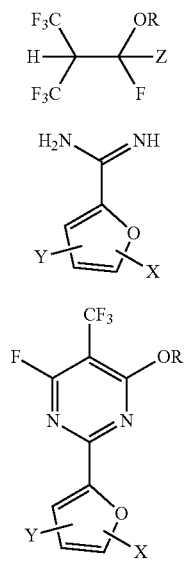

(d) reacting a fluoroisobutane derivative represented by the following formula (6) with a compound represented by the following formula (5) or a salt thereof to obtain a fluorine-containing pyrimidine compound represented by the following formula (2):

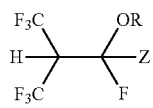

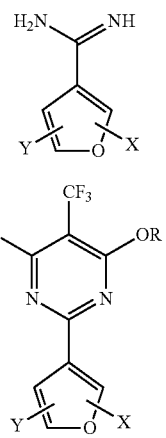

wherein in the formulae (1) and (2), and (4) to (6) above,
R represents a hydrocarbon group having 1 to 12 carbon atoms; and
X and Y each independently represent a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$, or $-CONA^1A^2$, and Z represents a halogen atom, $-OA^1$, $-SO_mA^1$ where m is an integer of 0 to 3, or $-NA^1A^2$, where $A^1$ and $A^2$ each independently represent a hydrogen atom or a hydrocarbon group having 1 to 10 carbon atoms.

5. The method for producing a fluorine-containing pyrimidine compound according to claim 3, wherein R is an alkyl group having 1 to 10 carbon atoms.

6. The method for producing a fluorine-containing pyrimidine compound according to claim 4, wherein R is an alkyl group having 1 to 10 carbon atoms.

* * * * *